United States Patent
Barbut et al.

(10) Patent No.: US 6,942,686 B1
(45) Date of Patent: Sep. 13, 2005

(54) REGULATION OF CEREBRAL BLOOD FLOW BY TEMPERATURE CHANGE-INDUCED VASODILATATION

(75) Inventors: Denise R. Barbut, New York, NY (US); Jon P. St. Germain, Elk River, MN (US); Joel R. Munsinger, Blaine, MN (US)

(73) Assignee: CoAxia, Inc., Maple Grove, MN (US)

( * ) Notice: Subject to any disclaimer, the term of this patent is extended or adjusted under 35 U.S.C. 154(b) by 211 days.

(21) Appl. No.: 10/286,940

(22) Filed: Nov. 1, 2002

(51) Int. Cl.[7] ............................................. A61F 7/00
(52) U.S. Cl. ..................................... 607/105; 607/109
(58) Field of Search ............................... 607/104–105, 607/108–114

(56) References Cited

U.S. PATENT DOCUMENTS

| | | | |
|---|---|---|---|
| 4,240,441 A * | 12/1980 | Khalil | 600/505 |
| 5,070,880 A * | 12/1991 | Gomez et al. | 600/452 |
| 5,195,942 A | 3/1993 | Weil et al. | |
| 5,247,928 A * | 9/1993 | Stilts, Jr. | 607/109 |
| 5,531,776 A | 7/1996 | Ward et al. | |
| 5,716,386 A | 2/1998 | Ward et al. | |
| 5,916,242 A * | 6/1999 | Schwartz | 607/113 |
| 5,957,963 A * | 9/1999 | Dobak, III | 607/104 |
| 6,161,547 A | 12/2000 | Barbut | |
| 6,190,304 B1 | 2/2001 | Downey et al. | |
| 6,223,069 B1 * | 4/2001 | Pfeiffer et al. | 600/431 |
| 6,231,551 B1 | 5/2001 | Barbut | |
| 6,296,654 B1 | 10/2001 | Ward | |
| 6,511,502 B2 * | 1/2003 | Fletcher | 607/109 |
| 6,599,312 B2 * | 7/2003 | Dobak, III | 607/105 |
| 6,682,552 B2 * | 1/2004 | Ramsden et al. | 607/109 |
| 6,743,196 B2 * | 6/2004 | Barbut et al. | 604/101.01 |

* cited by examiner

Primary Examiner—Roy D. Gibson
(74) Attorney, Agent, or Firm—O'Melveny & Myers LLP

(57) ABSTRACT

A method for enhancing cerebral blood flow in a patient. The patient's baseline cerebral blood flow is measured. An artery of the patient is cooled or warmed to produce vasodilatation of the artery. The artery is typically one or more of the left or right common carotid artery, left or right internal carotid artery, left or right middle cerebral artery, anterior cerebral artery, left or right vertebral artery, or basilar artery. Vasodilatation enhances cerebral blood flow. The enhanced cerebral blood flow is measured after cooling or warming the artery. The enhanced cerebral blood flow is compared to the baseline cerebral blood flow. Cooling or warming is then adjusted as needed to achieve a desired enhancement in cerebral blood flow. Devices for cooling and warming are also described.

101 Claims, 5 Drawing Sheets

REGULATION OF CEREBRAL BLOOD FLOW BY TEMPERATURE CHANGE-INDUCED VASODILATATION

FIELD OF THE INVENTION

The present invention relates to devices and methods for treating patients with focal cerebral ischemia such as acute ischemic stroke or vasospasm following subarachnoid hemorrhage or iatrogenic vasospasm, or global cerebral ischemia such as shock or cardiac arrest, and other conditions of reduced cerebral perfusion, and more particularly to devices and methods that enhance cerebral blood flow in a patient by reduced- or increased-temperature vasodilatation.

BACKGROUND OF THE INVENTION

Patients experiencing cerebral ischemia often suffer from disabilities ranging from transient neurological deficit to irreversible damage (stroke) or death. Cerebral ischemia, i.e., reduction or cessation of blood flow to the central nervous system, can be characterized as either global or focal. Global cerebral ischemia refers to reduction of blood flow within the cerebral vasculature resulting from systemic circulatory failure caused by, e.g., shock, cardiac failure, or cardiac arrest. Shock is the state in which failure of the circulatory system to maintain adequate cellular perfusion results in reduction of oxygen and nutrients to tissues. Within minutes of circulatory failure, tissues become ischemic, particularly in the heart and brain.

The two common forms of shock are cardiogenic shock, which results from severe depression of cardiac performance, and hemorrhagic shock, which results from trauma. The most frequent cause of cardiogenic shock is myocardial infarction with loss of substantial muscle mass. Pump failure can also result from acute myocarditis or from depression of myocardial contractility following cardiac arrest or prolonged cardiopulmonary bypass. Mechanical abnormalities, such as severe valvular stenosis, massive aortic or mitral regurgitation, and acutely acquired ventricular septal defects, can also cause cardiogenic shock by reducing cardiac output. Additional causes of cardiogenic shock include cardiac arrhythmia, such as ventricular fibrillation. Hemorrhagic shock is typically the result of penetrating injuries caused by, for example, traffic accidents and gunshot wounds. In this case, cardiac function is unimpaired and the cause of shock is circulatory blood loss.

Treatment of global cerebral ischemia involves treating the source of the systemic circulatory failure and ensuring adequate perfusion to the central nervous system. For example, treatment of cardiogenic shock due to prolonged cardiopulmonary bypass consists of cardiovascular support with the combination of inotropic agents such as dopamine, dobutamine, and intra-aortic balloon counterpulsation. Treatment of hemorrhagic shock consists of volume replacement and hemostasis. When these measures fail, supracoeliac aortic clamping is used. Vasoconstrictors, such as norepinephrine, are also administered systemically to maintain systolic blood pressure (ideally above 80 mmHg). Unfortunately, these agents produce pressure at the expense of flow, particularly blood flow to small vessels such as the renal arteries. The use of the vasoconstrictors is, therefore, associated with significant side effects, such as acute renal failure, congestive heart failure, and cardiac arrhythmias.

Focal cerebral ischemia refers to cessation or reduction of blood flow within the cerebral vasculature resulting from a partial or complete occlusion in the intracranial or extracranial cerebral arteries. Such occlusion typically results in stroke, a syndrome characterized by the acute onset of a neurological deficit that persists for at least 24 hours, reflecting focal involvement of the central nervous system. Stroke is the result of a disturbance of the cerebral circulation. Other causes of focal cerebral ischemia include vasospasm due to subarachnoid hemorrhage or iatrogenic intervention.

Traditionally, emergent management of acute ischemic stroke consists of mainly general supportive care, e.g. hydration, monitoring neurological status, blood pressure control, and/or anti-platelet or anti-coagulation therapy. Heparin has been administered to stroke patients with limited and inconsistent effectiveness. In some circumstances, the ischemia resolves itself over a period of time because some thrombi get absorbed into the circulation, or fragment and travel distally over a period of a few days. In June 1996, the Food and Drug Administration approved the use of tissue plasminogen activator (t-PA) or Activase®, for treating acute stroke. However, treatment with systemic t-PA is associated with increased risk of intracerebral hemorrhage and other hemorrhagic complications. Vasospasm may be partially responsive to vasodilating agents. The newly developing field of neurovascular surgery, which involves placing minimally invasive devices within the carotid arteries to physically remove the offending lesion, may provide a therapeutic option for these patients in the future, although this kind of manipulation may lead to vasospasm itself.

In both global and focal ischemia, patients develop neurologic deficits due to the reduction in cerebral blood flow. One treatment may include the use of devices to increase blood flow to the cerebral vasculature as the sole therapy. Alternatively, treatments include measures to increase blood flow to the cerebral vasculature to maintain viability of neural tissue, thereby increasing the length of time available for any adjunct interventional treatment and minimizing neurologic deficit while waiting for resolution of the ischemia. Augmenting blood flow to the cerebral vasculature is not only useful in treating occlusive or vasospastic cerebral ischemia, but may also be useful during interventional procedures, such as carotid angioplasty, stenting or endarterectomy, which might otherwise result in focal cerebral ischemia with or without focal vasospasm, and also cardiac procedures which may result in cerebral ischemia, such as cardiac catheterization, electrophysiologic studies, and angioplasty.

New devices and methods are thus needed for augmentation of cerebral blood flow in treating patients with either global or focal ischemia caused by reduced perfusion, thereby minimizing neurologic deficits.

SUMMARY OF THE INVENTION

The devices and methods described herein will find use in treating patients with cerebral ischemia, including focal cerebral ischemia, global cerebral ischemia (shock or cardiac arrest), acute ischemic stroke, cardiogenic shock, vasospasm (iatrogenic and spontaneous following subarachnoid hemorrhage), and other conditions of reduced cerebral perfusion. The devices and methods are used to enhance cerebral blood flow in a patient. Typically, the physician will measure a baseline cerebral blood flow on the patient who presents with acute ischemic stroke, cardiogenic shock, and other conditions of reduced cerebral perfusion. This measurement can be taken by transcranial Doppler, or any other suitable technique. Then, an artery of the patient is cooled to produce vasodilatation of the artery. In other embodiments, the artery is warmed to a temperature greater than normal body temperature (37° C.), in certain cases to a temperature greater than 38° C., greater than 39° C., or greater than 40° C.

In order to enhance cerebral blood flow, cooling or warming is typically carried out on one or more artery from the group of the right brachiocephalic trunk, left common carotid artery, left subclavian artery, right common carotid artery, right subclavian artery, left internal carotid artery, left middle cerebral artery, left anterior cerebral artery, right internal carotid artery, anterior cerebral arteries, anterior communicating artery, right posterior communicating artery, left posterior communicating artery, right posterior cerebral artery, left posterior cerebral artery, left vertebral artery, right vertebral artery, basilar artery, femoral artery, and brachial artery. Alternatively, a carotid bulb may be the target for cooling or warming to enhance cerebral blood flow.

Cooling or warming of the vessel can be accomplished by transcutaneous cooling or warming, by direct cooling or warming of the desired vessel, or by endovascular cooling or warming (infusion of cold or warm saline or by use of a cooling or heating probe at the end of a catheter). Transcutaneous cooling is generally accomplished by placing the cooling pad on the neck of the patient to cool one or more carotid arteries to produce vasodilatation of the one or more carotid arteries. The cooling pad may consist of a flexible cuff adapted to fit around the neck. In certain embodiments, the cuff includes a cooling zone that aligns with the desired vessel targeted for vasodilatation. In other embodiments, the cuff includes a fastening device adapted to fasten the cooling pad on a neck of the patient. The vessel may be cooled to 30° C. or below, 25° C. or below, 20° C. or below, 15° C. or below, 10° C. or below, or 5° C. or below.

Temperature-mediated vasodilatation will find application in carotid stenting and intracranial procedures where vasospasm is likely to occur. The interventional catheter can be equipped with a lumen for infusion of cold or warm saline or other biocompatible fluid. Alternatively, the interventional catheter may be equipped with a cooling or heating probe. In other embodiments, transcutaneous cooling or heating may be accomplished during carotid stenting and intracranial procedures where vasospasm is likely to occur. In still other embodiments, systemic cooling is accomplished during carotid stenting and intracranial procedures.

In a typical stenting procedure, a guidewire is advanced to a region of interest within one of the right brachiocephalic trunk, left common carotid artery, left subclavian artery, right common carotid artery, right subclavian artery, left internal carotid artery, left middle cerebral artery, left anterior cerebral artery, right internal carotid artery, anterior cerebral arteries, anterior communicating artery, right posterior communicating artery, left posterior communicating artery, right posterior cerebral artery, left posterior cerebral artery, left vertebral artery, right vertebral artery, basilar artery, femoral artery, and brachial artery. The catheter is then advanced to the region of interest over the guidewire. The position of the lesion is identified by angiography. The stent is deployed at the region of interest to dilate the lesion. Cooling or warming is performed before and/or after stent deployment in order to prevent or treat vasospasm. In this manner, iatrogenic vasospasm, spontaneous vasospasm, and iatrogenic shock may be avoided. After the vessel has stabilized, the catheter and guidewire are removed from the patient.

Cooling or warming the artery causes vasodilatation, which increases cerebral blood flow. The physician then measures an enhanced cerebral blood flow after cooling the artery, and compares the enhanced cerebral blood flow to the baseline cerebral blood flow. The level of cooling can then be adjusted to achieve a desired increase in cerebral blood flow. The desired increase in cerebral blood flow may be 5 percent or more, 15 percent or more, 25 percent or more, 35 percent or more, 45 percent or more, up to 50 percent, 55 percent or more, up to 60 percent, 65 percent or more, up to 70 percent, 75 percent or more, up to 80 percent, 85 percent or more, 95 percent or more, or 100 percent or more. In some cases the desired increase will be 5–50 percent. In other cases the desired increase will be 10–30 percent. Increased cerebral blood flow will typically be observed within one minute of cooling or warming the artery. Cooling is maintained for about 10 minutes, 15 minutes, 20 minutes, or longer.

If autoregulatory effects are noted to produce a diminished cerebral blood flow, then cooling is discontinued, and the artery is allowed to warm to at or near normal body temperature. Then, cooling the artery of the patient is repeated to again produce vasodilatation.

DETAILED DESCRIPTION

The devices and methods disclosed herein are to be used in treating patients suffering from global cerebral ischemia due to systemic circulatory failure, and focal cerebral ischemia due to thromboembolic occlusion or vasospasm of the cerebral vasculature. However, it will be understood that the devices and methods can be used in other medical conditions.

Figure 1:
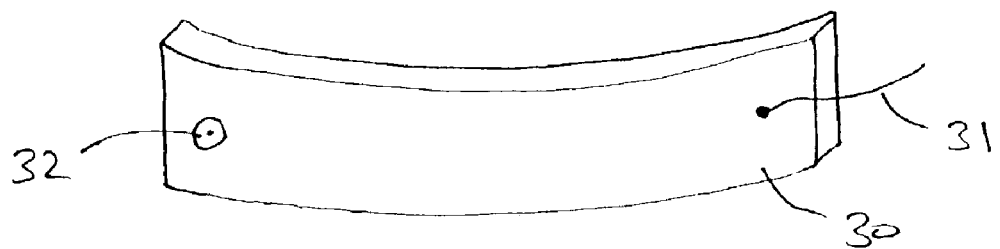
FIG. 1 depicts a cooling or heating pad for use in the present invention.
Figure 2:
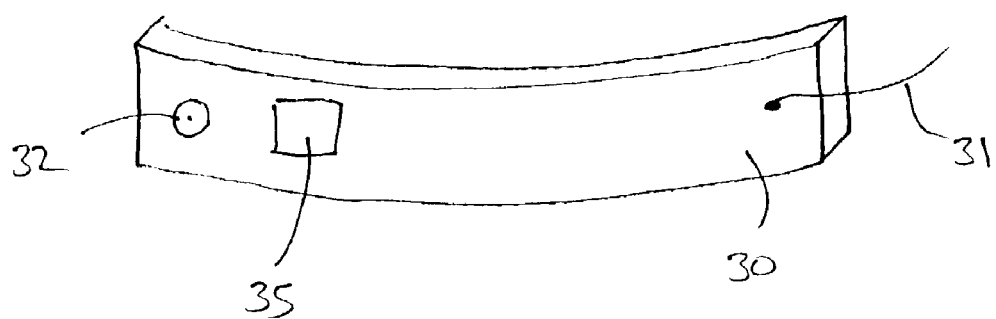
FIG. 2 depicts a cooling or heating pad having a localized cooling zone.

A cooling or warming device in accordance with the present invention is depicted in FIG. 1. Cooling pad 30 comprises a flexible band of material that can be placed around the neck and comfortably conforms to the skin. Strap 31 attaches to button 32 to hold cooling pad 30 in place during use. The cooling pad can be made of a thermal gel material that is cooled in a refrigerator or freezer, the gel being packed in a plastic sleeve. In certain embodiments, the plastic sleeve will be placed within a felt material to avoid freezer burn on contact with the skin and to give a more comfortable fit for extended use. In other embodiments, the cooling pad comprises a compartment of water and a compartment of ammonium nitrate, both compartments contained within a plastic sleeve. When the compartments are broken by squeezing, the water mixes with the ammonium nitrate to form a reduced-temperature mixture. One commercially available product is the Kwik-Kold® Instant Ice Pack by Baxter. As an alternative to this chemical cooling system, electrical cooling and water cooling may be employed. The cooling pad should be capable of reaching and retaining for several minutes a temperature of 30° C. or below, 25° C. or below, 20° C. or below, 15° C. or below, 10° C. or below, or 5° C. or below.

Where the location of desired cooling is known, then localized cooling or warming may be employed using a cooling pad as depicted in FIG. 2. Cooling pad 30 contains localized cooling zone 35. Using this device, the majority of cooling pad 30 is maintained at or near normal body temperature. Localized cooling, and therefore vasodilatation, of a desired artery is achieved by placement of cooling pad 30 on the patient's neck so that localized cooling zone 35 is aligned and placed over the desired artery.

Figure 3:
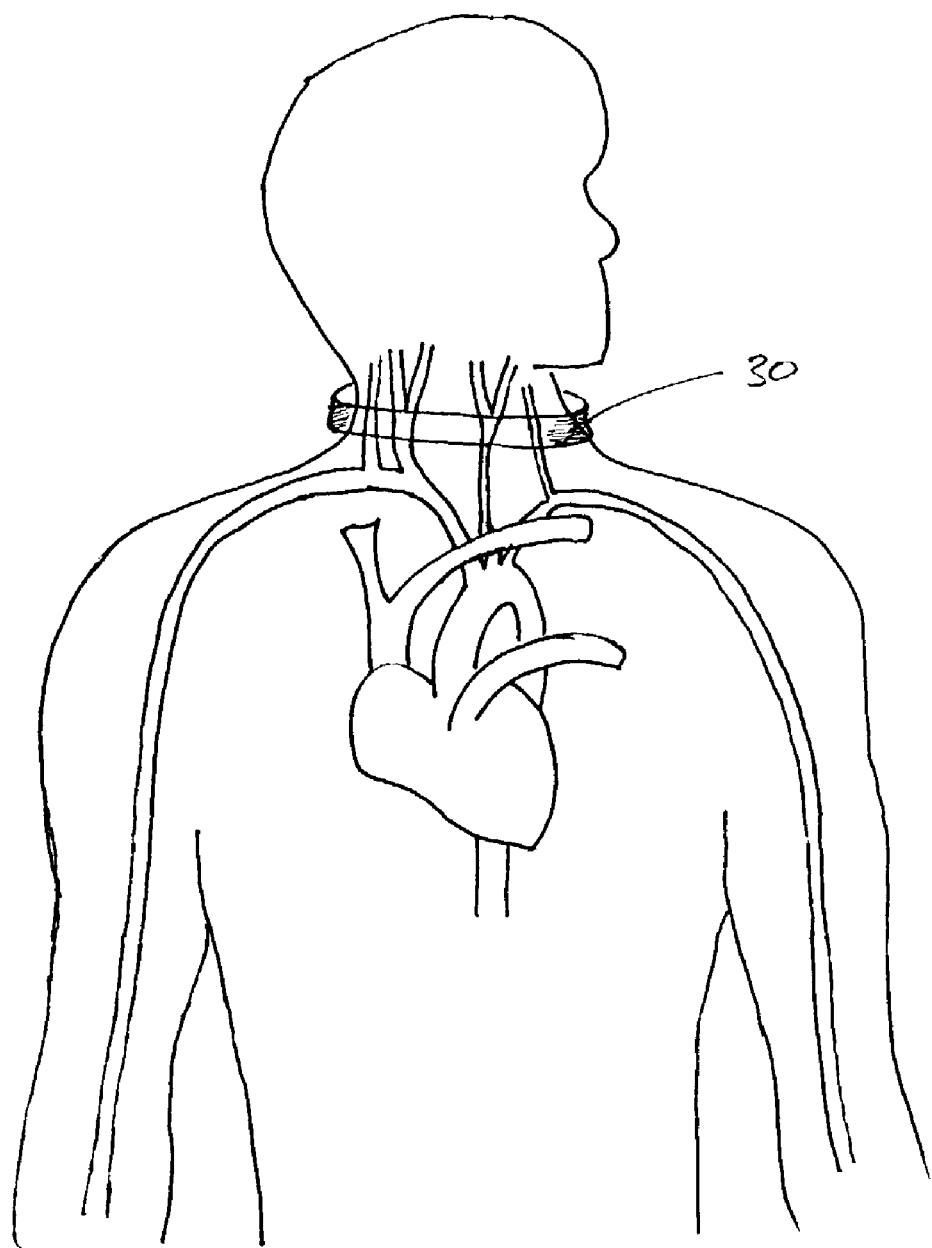
FIG. 3 depicts the device of FIG. 1 in place on the patient's neck to effect cooling or warming of a carotid or vertebral artery.

In use, cooling or heating pad 30 is worn on the neck of a patient, as shown in FIG. 3. Strap 31 is attached to button 32 to hold the cooling or heating pad in place. When localized cooling or heating is employed, zone 35 must be aligned with the desired artery. Upon cooling or heating, vessel diameter may be increased within seconds by 10 percent or more, 13 percent or more, 16 percent or more, or as much as 20 percent or more. Upon cooling or heating the common carotid artery, the ipsilateral middle cerebral artery flow velocity increases by 20 percent or more, 25 percent or more, 30 percent or more, 40 percent or more, or 50 percent or more. Moreover, due to a neurogenic response, contralateral middle cerebral artery flow velocity increases by 10 percent or more, 15 percent or more, or 20 percent or more.

On cooling or warming, peak systolic velocity, end diastolic velocity, and mean velocity increases as well. Pulsatility index is unchanged. Heart rate typically increases as well due to a neurogenic response to cooling. Increased heart rate produces increased cardiac output, which increases cerebral blood flow. If the cooling pad is removed for up to 30 seconds, cerebral blood flow does not change. Thus, intermittent stoppage of cooling can be employed to reduce discomfort.

The vasodilatory effect persists for 10 minutes or more, 15 minutes or more, or 20 minutes or more. At that time, cooling or warming is removed, and the vessel is permitted to return to a temperature at or near normal body temperature. Cooling pad 30 is then reapplied as shown in FIG. 3 to again cause vasodilatation and increased cerebral blood flow.

Figure 4:
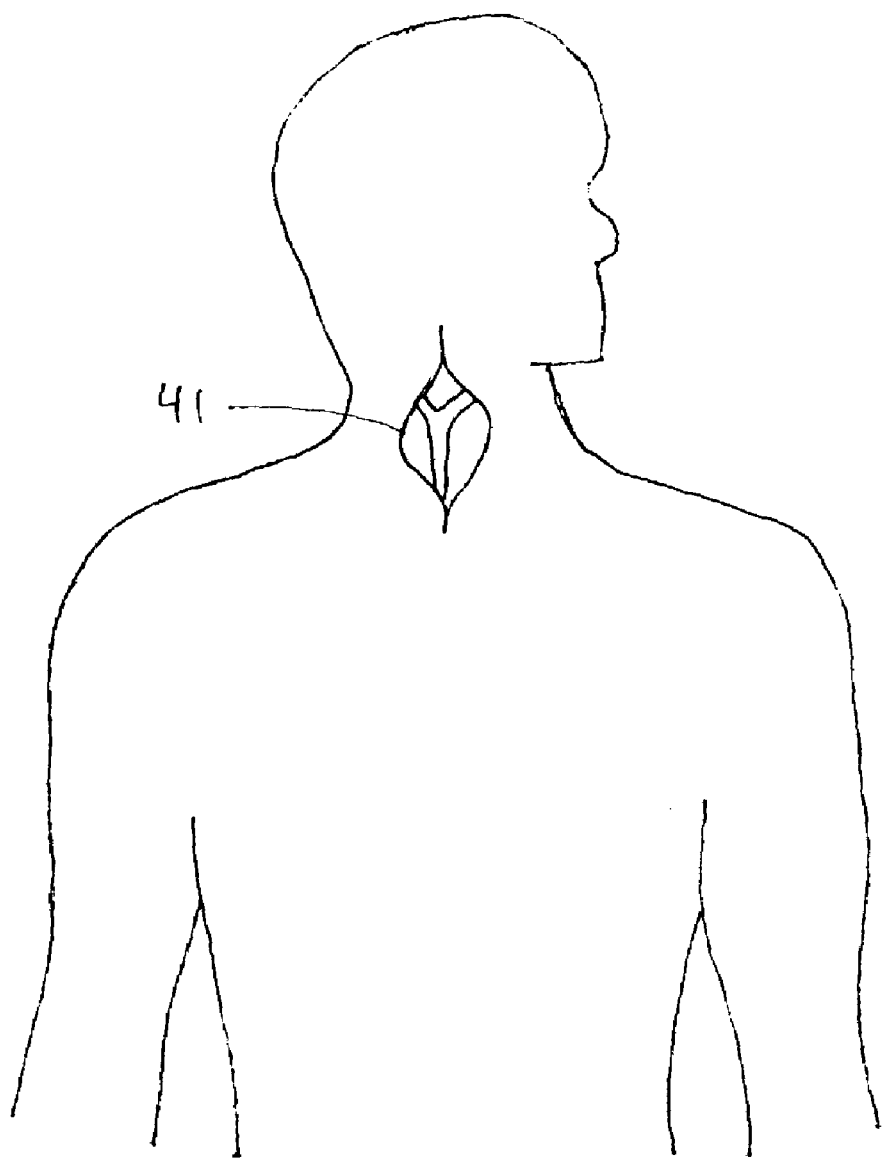
FIG. 4 depicts the direct cooling or warming of a carotid artery.

In another method as depicted in FIG. 4, an incision 41 is made, in this case on the neck, to expose the arteries for cooling or warming. Ice cold saline, or other suitable solution, is dripped on the right or left common carotid artery, right or left internal carotid artery, and/or other arteries discussed herein. Vasodilatation occurs, and this causes an increase in vessel diameter, cerebral blood flow, ipsilateral middle cerebral artery flow velocity, peak systolic velocity, end diastolic velocity, and mean velocity. Pulsatility index is unchanged.

The vasodilatory effect persists for 10 minutes or more, 15 minutes or more, or 20 minutes or more. At that time, the cold drip is discontinued, and the vessel is permitted to return to a temperature at or near normal body temperature. Cold solution is then dripped on the artery to again cause vasodilatation and increased cerebral blood flow.

Figure 5:
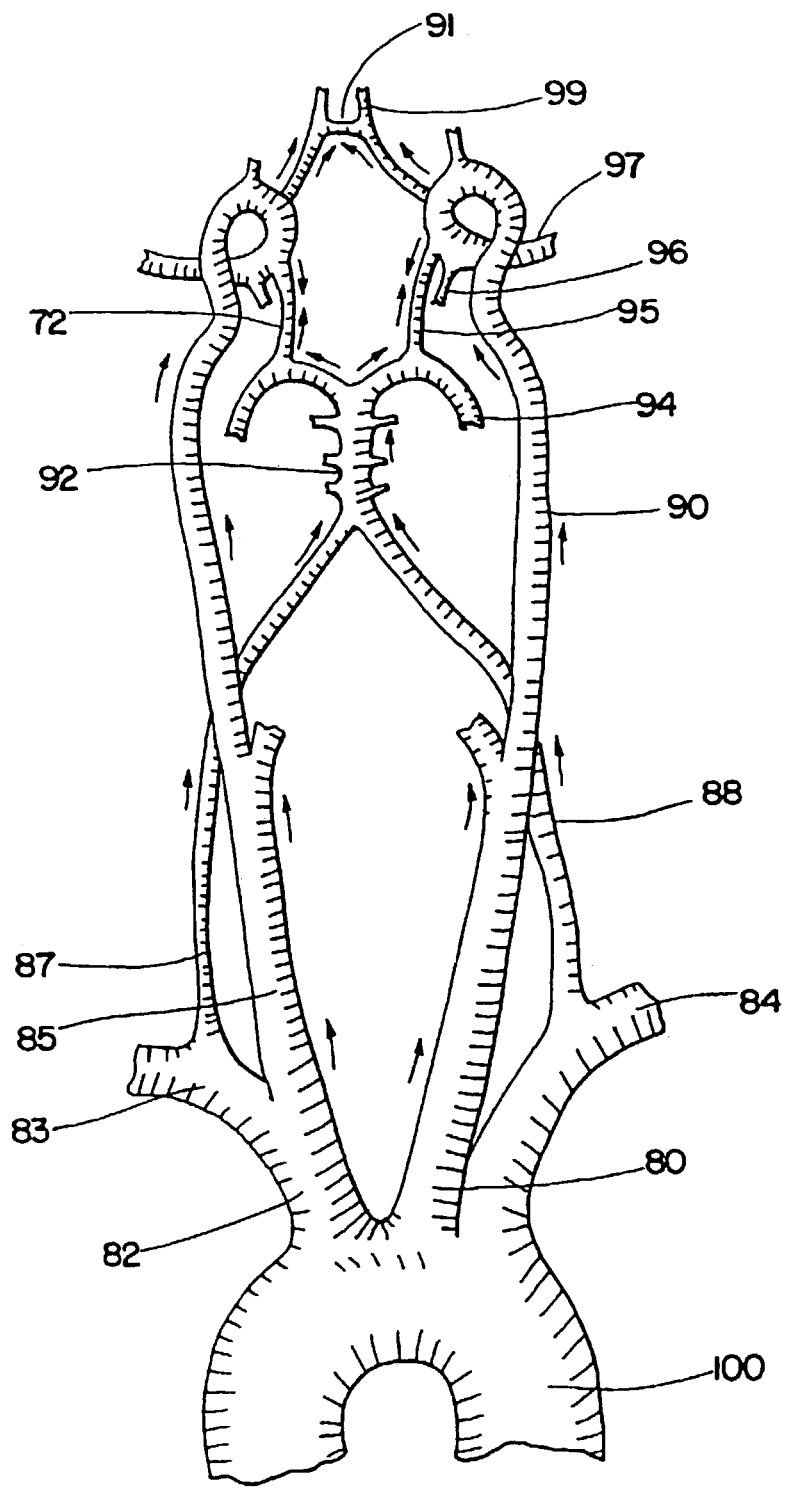
FIG. 5 depicts cerebral vascular anatomy showing the arteries on which temperature-mediated vasodilatation may be carried out.

The cooling or warming methods and devices described herein may be applied to any of the arteries depicted in FIG. 5 to increase cerebral blood flow. FIG. 5 depicts normal cerebral circulation and formation of Circle of Willis. Aorta 100 gives rise to right brachiocephalic trunk 82, left common carotid artery (CCA) 80, and left subclavian artery 84. The brachiocephalic artery further branches into right common carotid artery 85 and right subclavian artery 83. The left CCA gives rise to left internal carotid artery (ICA) 90 which becomes left middle cerebral artery (MCA) 97 and left anterior cerebral artery (ACA) 99. Anteriorly, the Circle of Willis is formed by the internal carotid arteries, the anterior cerebral arteries, and anterior communicating artery 91 which connects the two ACAs. The right and left ICA also send right posterior communicating artery 72 and left posterior communicating artery 95 to connect, respectively, with right posterior cerebral artery (PCA) 74 and left PCA 94. The two posterior communicating arteries and PCAs, and the origin of the posterior cerebral artery from basilar artery 92 complete the circle posteriorly.

Figure 6:
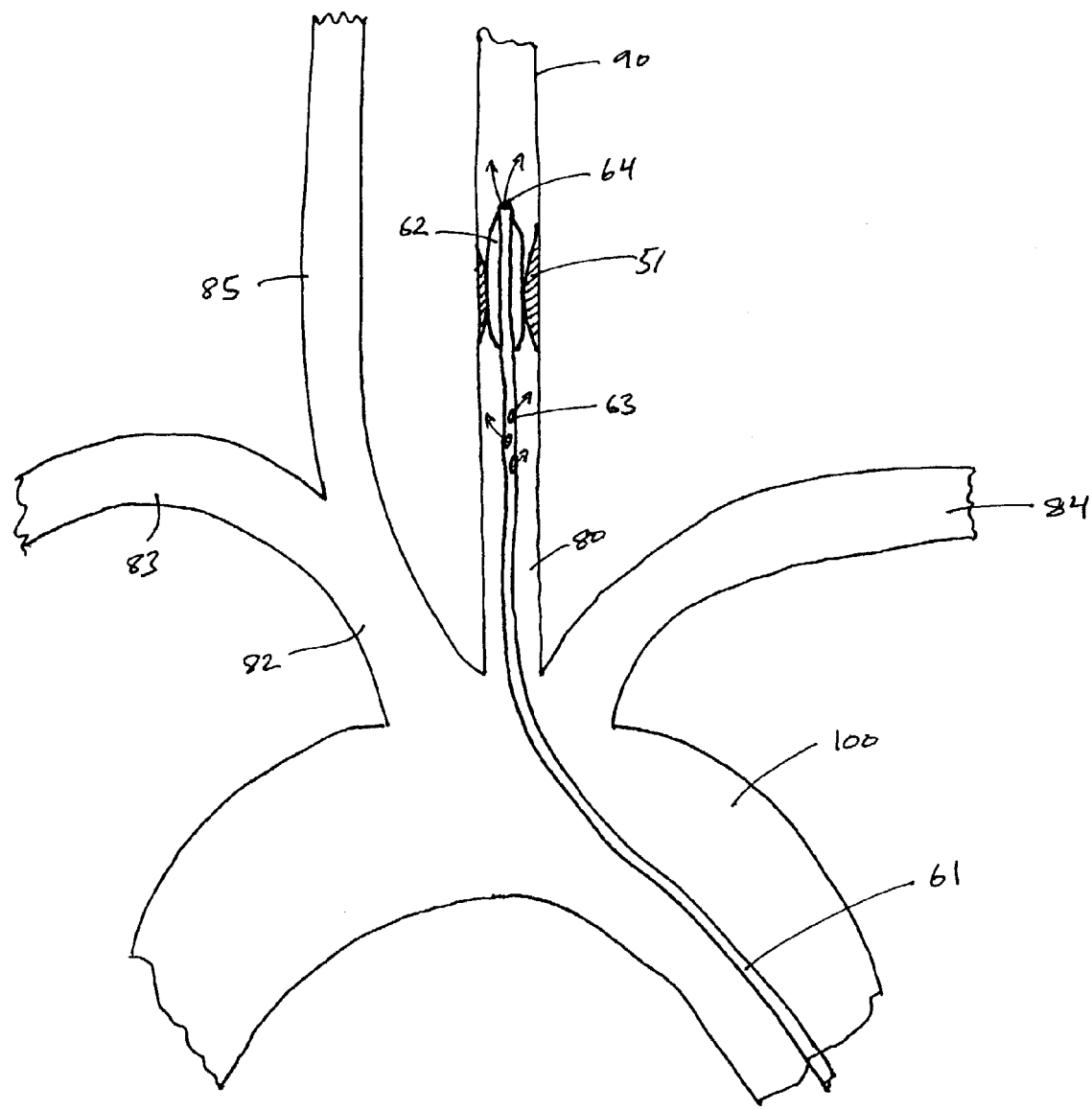
FIG. 6 depicts an interventional procedure with temperature-mediated vasodilatation to prevent vasospasm.

Endovascular temperature-induced vasodilatation is depicted in FIG. 6. Interventional catheter 61 (here an angioplasty or stenting catheter) carries balloon 62 in a distal region of catheter 61. Catheter 61 may be equipped with infusion ports 63 and/or 64. In other embodiments catheter 61 carries a cooling or heating probe (not shown). Balloon 62 is positioned within lesion 51 in left common carotid artery 80. Cold or warm solution is infused before, during, and/or after inflation of balloon 62. In this manner, the operator treats or prevents vasospasm during angioplasty or while installing a stent.

Although the foregoing invention has, for the purposes of clarity and understanding, been described in some detail by way of illustration and example, it will be obvious that certain changes and modifications may be practiced which will still fall within the scope of the appended claims.

What is claimed is:

1. A method for enhancing cerebral blood flow in a patient, comprising the steps of:
   measuring a baseline cerebral blood flow;
   cooling a common carotid artery of the patient to produce vasodilatation of the common carotid artery;
   measuring an enhanced cerebral blood flow after cooling the common carotid artery; and
   comparing the enhanced cerebral blood flow to the baseline cerebral blood flow.

2. The method of claim 1, wherein the common carotid artery is cooled to 25° C. or lower.

3. The method of claim 1, further comprising the step of adjusting the level of cooling to achieve a desired increase in cerebral blood flow.

4. The method of claim 3, wherein the desired increase in cerebral blood flow is 5 percent or more.

5. The method of claim 3, wherein the desired increase in cerebral blood flow is 5–50 percent.

6. The method of claim 3, wherein the desired increase in cerebral blood flow is 10–30 percent.

7. The method of claim 1, wherein the cooling is accomplished by transcutaneous cooling.

8. The method of claim 1, further comprising the step of exposing the common carotid artery by cut down to the common carotid artery.

9. The method of claim 1, wherein the cooling is accomplished endovascularly.

10. The method of claim 1, wherein the cooling is maintained for about 15 minutes.

11. The method of claim 1, further comprising the steps of:
   discontinuing cooling, whereby the common carotid artery warms to at or near normal body temperature; and
   cooling the common carotid artery of the patient again to produce vasodilatation of the common carotid artery.

12. The method of claim 11, further comprising the steps of repeating the step of discontinuing cooling, whereby the common carotid artery warms to at or near normal body temperature, and repeating the step of cooling the common carotid artery of the patient again to produce vasodilatation of the common carotid artery.

13. The method of claim 1, wherein the cooling is performed on the right common carotid artery or carotid bulb.

14. The method of claim 1, wherein the cooling is performed on the left common carotid artery or carotid bulb.

15. The method of claim 1, wherein cerebral blood flow is measured by transcranial Doppler or carotid Doppler.

16. The method of claim 1, wherein the common carotid artery is cooled to 25° C. or lower.

17. The method of claim 1, further comprising the step of adjusting the level of cooling to achieve a desired increase in cerebral blood flow.

18. The method of claim 17, wherein the desired increase in cerebral blood flow is 5 percent or more.

19. The method of claim 17, wherein the desired increase in cerebral blood flow is 5–50 percent.

20. The method of claim 17, wherein the desired increase in cerebral blood flow is 10–30 percent.

21. The method of claim 1, wherein the cooling is accomplished by transcutaneous cooling.

22. The method of claim 1, further comprising the step of exposing the common carotid artery by cut down to the common carotid artery.

23. The method of claim 1, wherein the cooling is accomplished endovascularly.

24. The method of claim 1, wherein the cooling is maintained for about 15 minutes.

25. The method of claim 1, further comprising the steps of:
    discontinuing cooling, whereby the common carotid artery warms to at or near normal body temperature; and
    cooling the common carotid artery of the patient again to produce vasodilatation of the common carotid artery.

26. The method of claim 25, further comprising the steps of repeating the step of discontinuing cooling, whereby the common carotid artery warms to at or near normal body temperature, and repeating the step of cooling the common carotid artery of the patient again to produce vasodilatation of the common carotid artery.

27. The method of claim 1, wherein the cooling is performed on the right common carotid artery or carotid bulb.

28. The method of claim 1, wherein the cooling is performed on the left common carotid artery or carotid bulb.

29. The method of claim 1, wherein cerebral blood flow is measured by transcranial Doppler or carotid Doppler.

30. A method for enhancing cerebral blood flow in a patient, comprising the steps of:
    measuring a baseline cerebral blood flow; cooling an internal carotid artery of the patient to produce vasodilatation of the internal carotid artery;
    measuring an enhanced cerebral blood flow after cooling the internal carotid artery; and
    comparing the enhanced cerebral blood flow to the baseline cerebral blood flow.

31. The method of claim 30, wherein the internal carotid artery is cooled to 25° C. or lower.

32. The method of claim 30, further comprising the step of adjusting the level of cooling to achieve a desired increase in cerebral blood flow.

33. The method of claim 32, wherein the desired increase in cerebral blood flow is 5 percent or more.

34. The method of claim 32, wherein the desired increase in cerebral blood flow is 5–50 percent.

35. The method of claim 32, wherein the desired increase in cerebral blood flow is 10–30 percent.

36. The method of claim 30, wherein the cooling is accomplished by transcutaneous cooling.

37. The method of claim 30, further comprising the step of exposing the internal carotid artery by cut down to the internal carotid artery.

38. The method of claim 30, wherein the cooling is accomplished endovascularly.

39. The method of claim 30, wherein the cooling is maintained for about 15 minutes.

40. The method of claim 30, further comprising the steps of:
    discontinuing cooling, whereby the internal carotid artery warms to at or near normal body temperature; and
    cooling the internal carotid artery of the patient again to produce vasodilatation of the internal carotid artery.

41. The method of claim 40, further comprising the steps of repeating the step of discontinuing cooling, whereby the internal carotid artery warms to at or near normal body temperature, and repeating the step of cooling the internal carotid artery of the patient again to produce vasodilatation of the internal carotid artery.

42. The method of claim 30, wherein the cooling is performed on the right internal carotid artery.

43. The method of claim 30, wherein the cooling is performed on the left internal carotid artery.

44. The method of claim 30, wherein cerebral blood flow is measured by transcranial Doppler.

45. The method of claim 30, wherein the internal carotid artery is cooled to 25° C. or lower.

46. The method of claim 30, further comprising the step of adjusting the level of cooling to achieve a desired increase in cerebral blood flow.

47. The method of claim 46, wherein the desired increase in cerebral blood flow is 5 percent or more.

48. The method of claim 46, wherein the desired increase in cerebral blood flow is 5–50 percent.

49. The method of claim 46, wherein the desired increase in cerebral blood flow is 10–30 percent.

50. The method of claim 30, wherein the cooling is accomplished by transcutaneous cooling.

51. The method of claim 30, further comprising the step of exposing the internal carotid artery by cut down to the internal carotid artery.

52. The method of claim 30, wherein the cooling is accomplished endovascularly.

53. The method of claim 30, wherein the cooling is maintained for about 15 minutes.

54. The method of claim 30, further comprising the steps of:
    discontinuing cooling, whereby the internal carotid artery warms to at or near normal body temperature; and
    cooling the internal carotid artery of the patient again to produce vasodilatation of the internal carotid artery.

55. The method of claim 54, further comprising the steps of repeating the step of discontinuing cooling, whereby the internal carotid artery warns to at or near normal body temperature, and repeating the step of cooling the internal carotid artery of the patient again to produce vasodilatation of the internal carotid artery.

56. The method of claim 30, wherein the cooling is performed on the right internal carotid artery.

57. The method of claim 30, wherein the cooling is performed on the left internal carotid artery.

58. The method of claim 30, wherein cerebral blood flow is measured by transcranial Doppler.

59. A method for enhancing cerebral blood flow in a patient, comprising the steps of:
measuring a baseline cerebral blood flow;
cooling a vertebral artery of the patient to produce vasodilatation of the vertebral artery;
measuring an enhanced cerebral blood flow after cooling the vertebral artery; and
comparing the enhanced cerebral blood flow to the baseline cerebral blood flow.

60. The method of claim 59, wherein the vertebral artery is cooled to 25° C. or lower.

61. The method of claim 59, further comprising the step of adjusting the level of cooling to achieve a desired increase in cerebral blood flow.

62. The method of claim 61, wherein the desired increase in cerebral blood flow is 5 percent or more.

63. The method of claim 61, wherein the desired increase in cerebral blood flow is 5–50 percent.

64. The method of claim 61, wherein the desired increase in cerebral blood flow is 10–30 percent.

65. The method of claim 59, wherein the cooling is accomplished by transcutaneous cooling.

66. The method of claim 59, further comprising the step of exposing the vertebral artery by cut down to the vertebral artery.

67. The method of claim 59, wherein the cooling is accomplished endovascularly.

68. The method of claim 59, wherein the cooling is maintained for about 15 minutes.

69. The method of claim 59, further comprising the steps of:
discontinuing cooling, whereby the vertebral artery warms to at or near normal body temperature; and
cooling the vertebral artery of the patient again to produce vasodilatation of the vertebral artery.

70. The method of claim 69, further comprising the steps of repeating the step of discontinuing cooling, whereby the vertebral artery warms to at or near normal body temperature, and repeating the step of cooling the vertebral artery of the patient again to produce vasodilatation of the vertebral artery.

71. The method of claim 31, wherein the cooling is performed on the right vertebral artery.

72. The method of claim 31, wherein the cooling is performed on the left vertebral artery.

73. The method of claim 31, wherein cerebral blood flow is measured by transcranial Doppler.

74. The method of claim 59, wherein the vertebral artery is cooled to 25° C. or lower.

75. The method of claim 59, further comprising the step of adjusting the level of cooling to achieve a desired increase in cerebral blood flow.

76. The method of claim 75, wherein the desired increase in cerebral blood flow is 5 percent or more.

77. The method of claim 75, wherein the desired increase in cerebral blood flow is 5–50 percent.

78. The method of claim 75, wherein the desired increase in cerebral blood flow is 10–30 percent.

79. The method of claim 59, wherein the cooling is accomplished by transcutaneous cooling.

80. The method of claim 59, further comprising the step of exposing the vertebral artery by cut down to the vertebral artery.

81. The method of claim 59, wherein the cooling is accomplished endovascularly.

82. The method of claim 59, wherein the cooling is maintained for about 15 minutes.

83. The method of claim 59, further comprising the steps of:
discontinuing cooling, whereby the vertebral artery warms to at or near normal body temperature; and
cooling the vertebral artery of the patient again to produce vasodilatation of the vertebral artery.

84. The method of claim 83, further comprising the steps of repeating the step of discontinuing cooling, whereby the vertebral artery warms to at or near normal body temperature, and repeating the step of cooling the vertebral artery of the patient again to produce vasodilatation of the vertebral artery.

85. The method of claim 59, wherein the cooling is performed on the right vertebral artery.

86. The method of claim 59, wherein the cooling is performed on the left vertebral artery.

87. The method of claim 59, wherein cerebral blood flow is measured by transcranial Doppler.

88. A method for enhancing cerebral blood flow in a patient, comprising the steps of:
providing a cooling pad adapted for placement on a neck of the patient;
measuring a baseline cerebral blood flow;
placing the cooling pad on the neck of the patient to cool one or more carotid arteries to produce vasodilatation of the one or more carotid arteries; and
measuring an enhanced cerebral blood flow after cooling the one or more carotid arteries.

89. The method of claim 88, wherein the one or more carotid arteries are cooled to 25° C. or lower.

90. The method of claim 88, further comprising the step of comparing the enhanced cerebral blood flow to the baseline cerebral blood flow.

91. The method of claim 88, further comprising the step of adjusting the level of cooling to achieve a desired increase in cerebral blood flow.

92. The method of claim 91, wherein the desired increase in cerebral blood flow is 5 percent or more.

93. The method of claim 91, wherein the desired increase in cerebral blood flow is 5–50 percent.

94. The method of claim 91, wherein the desired increase in cerebral blood flow is 10–30 percent.

95. The method of claim 88, wherein the cooling pad is a flexible cuff adapted to fit around the neck.

96. The method of claim 95, wherein the cuff includes a cooling zone that aligns with a vessel selected from the group consisting of right brachiocephalic trunk, left common carotid artery, left subclavian artery, right common carotid artery, right subclavian artery, left internal carotid artery, left middle cerebral artery, left anterior cerebral artery, right internal carotid artery, anterior cerebral arteries, anterior communicating artery, right posterior communicating artery, left posterior communicating artery, right posterior cerebral artery, left posterior cerebral artery, carotid bulb, and basilar artery.

97. A method for enhancing cerebral blood flow in a patient, comprising the steps of:
measuring a baseline cerebral blood flow;
warming an artery of the patient selected from the group consisting of a right brachiocephalic trunk, left common carotid artery, left subclavian artery, right common carotid artery, right subclavian artery, left internal carotid artery, left middle cerebral artery, left anterior cerebral artery, right internal carotid artery, anterior cerebral arteries, anterior communicating artery, right posterior communicating artery, left posterior communicating artery, right posterior cerebral artery, left posterior cerebral artery, carotid bulb, and basilar artery, to produce vasodilatation of the artery;

measuring an enhanced cerebral blood flow after warming the artery; and comparing the enhanced cerebral blood flow to the baseline cerebral blood flow.

98. The method of claim 56, wherein the artery is warmed to 38° C. or higher.

99. The method of claim 97, wherein the artery is warmed to 38° C. or higher.

100. A method for enhancing cerebral blood flow in a patient, comprising the steps of:

providing a heating pad adapted for placement on a neck of the patient;

measuring a baseline cerebral blood flow;

placing the heating pad on the neck of the patient to warm one or more carotid arteries to produce vasodilatation of the one or more carotid arteries; and measuring an enhanced cerebral blood flow after warming the one or more carotid arteries.

101. The method of claim 58, wherein the carotid artery is warmed to 38° C. or higher.

* * * * *